United States Patent [19]
Dake et al.

[11] Patent Number: 4,927,418
[45] Date of Patent: May 22, 1990

[54] CATHETER FOR UNIFORM DISTRIBUTION OF THERAPEUTIC FLUIDS

[75] Inventors: Michael D. Dake, Miami, Fla.; Mark A. Maguire, San Jose, Calif.

[73] Assignee: Advanced Cardiovascular Systems, Inc., Santa Clara, Calif.

[21] Appl. No.: 295,088

[22] Filed: Jan. 9, 1989

[51] Int. Cl.$^5$ ............................................. A61M 5/325
[52] U.S. Cl. ................................. 604/264; 604/280
[58] Field of Search ............... 604/264, 258, 275, 280, 604/281, 282, 43, 51, 54, 48, 49

[56] References Cited

U.S. PATENT DOCUMENTS

| | | |
|---|---|---|
| 4,329,994 | 5/1982 | Cooper . |
| 4,543,089 | 9/1985 | Moss . |
| 4,543,987 | 9/1985 | Sommercorn et al. . |
| 4,577,637 | 3/1986 | Mueller, Jr. . |
| 4,682,978 | 7/1987 | Martin . |
| 4,717,379 | 1/1988 | Ekholmer . |
| 4,769,005 | 9/1988 | Ginsburg et al. ............... 604/264 X |
| 4,795,439 | 1/1989 | Guest ............................. 604/264 X |

*Primary Examiner*—John D. Yasko
*Attorney, Agent, or Firm*—Fulwider, Patton, Lee & Utecht

[57] ABSTRACT

A vascular catheter for delivering a uniform flow of therapeutic fluid over a length of the catheter. The catheter is particularly suitable for delivering thrombolytic agents to a thrombus or clot in a patient's arterial system. In a preferred embodiment, the catheter has a relatively thick-walled tubular body with a central lumen for advancement over a guidewire and a plurality of fluid delivering lumens disposed within the relatively thick wall. Each of the smaller lumens has a single flow passageway to discharge therapeutic fluid to the exterior of the catheter.

14 Claims, 1 Drawing Sheet

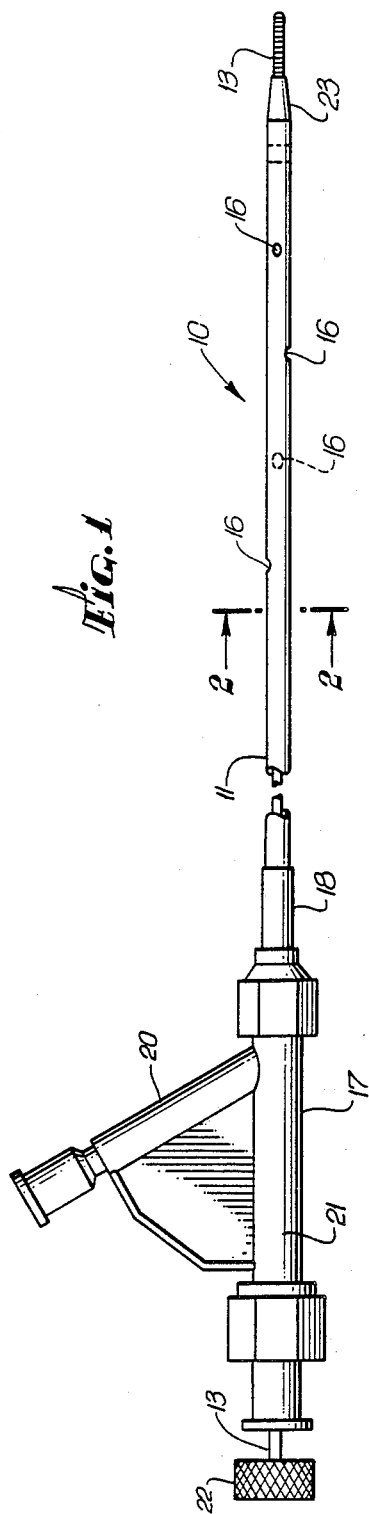
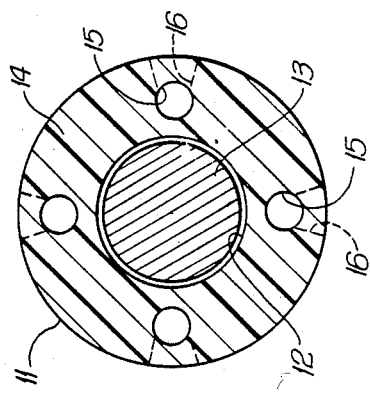
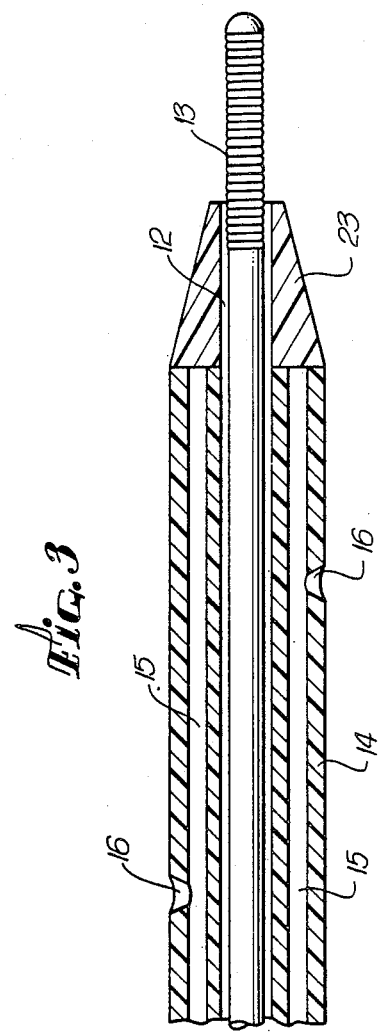

CATHETER FOR UNIFORM DISTRIBUTION OF THERAPEUTIC FLUIDS

BACKGROUND OF THE INVENTION

This invention generally relates to a vascular catheter for the delivery of therapeutic fluids and particularly for the uniform delivery of thrombolytic fluids to a vascular location of a patient having a thrombus or clot.

The utilization of therapeutic fluids containing tissue plasminogen activator (TPA), urokinase and streptokiase have shown promise in the treatment of thrombus or clots in a patient's arterial have been limited by the fact that the patient's total body is medicated in order to effect sites in the patient's arterial vasculature. Direct delivery of thrombolytic fluids to the target tissue would allow for a much more effective treatment procedure. However, there have been no effective delivery systems available. More particularly, there has not been available a delivery system which can deliver a uniform flow of such therapeutic fluids along the length of a thrombus in a patient's artery. The present invention satisfies that need.

SUMMARY OF THE INVENTION

The present invention is directed to a multilumen vascular catheter which provides a more uniform and thus more effective delivery of fluids containing drugs or therapeutic agents to a desired vasculature location.

The vascular catheter in accordance with the present invention generally comprises an elongated tubular body having a relatively large inner lumen, with an axial opening in the distal end thereof, which is adapted to receive a guidewire and a plurality of relatively small lumens which direct fluid containing drugs, therapeutic agents and the like to the distal portion of the tubular body. Each of the smaller lumens has a single flow passageway in fluid communication therewith which extends through the wall of the tubular body and is open to the exterior of the catheter to discharge fluid therefrom. The flow passageways are spaced longitudinally along a length of the tubular body and have essentially equivalent minimum transverse cross-sections to provide a uniform fluid flow over said length. Preferably, the passageways are spirally arranged to ensure uniform flow around the periphery of the catheter.

In a preferred embodiment the tubular body has a relatively thick walled cylindrical shape with the relatively large diameter lumen adapted to receive the guidewire, being centrally disposed. A plurality small diameter lumens are provided which extend longitudinally through the relatively thick wall of the tubular body.

The proximal end of the catheter is provided with an adapter which directs fluids through one arm thereof to the small diameter lumens and one arm to direct a guidewire through the relatively large diameter. If desired, each of the small diameter lumens can be provided with separate fluid sources in order to more accurately deliver fluid therethrough.

The minimum transverse cross-sectional area of the flow passages ranges from about 0.00005 in$^2$ to about 0.002 in$^2$ for fluid flows of about 0.1 to about 1.5 cc's per minute at lumen pressures of about 2 to about 5 psi. The cross-sectional areas can be varied depending upon the fluid flow rate desired, the viscosity and density of the fluid and the fluid pressure available. The number of flow passageways can number from 2 to up to 12 or more, but generally only 4–8 are needed. The spacing between the passageways is preferably uniform but may vary from about 0.5 to about 5 cm.

Typically a guidewire is directed through a patient's arterial system to a location therein having a thrombus or clot which occludes or partially occludes the artery. The distal portion of the guidewire is advanced through the clot, then the vascular catheter of the invention is mounted onto the guidewire and advanced thereover until the distal portion of the catheter having the flow passageways in the wall thereof is in position within the thrombus. Fluid containing thrombolytic agents such as urokinase, streptokinase, tissue plasminogen activator (TPA) and the like is then directed through the small diameter lumens and the flow passageway associated with each of such lumens to the exterior of the catheter into the thrombus. The fluid flow rate is relatively low as is the pressure to allow the fluid to penetrate through and dissolve the clot. The flow out of the passageways is uniform over the length of the catheter containing such passageways. In this manner, a uniform thrombolysis is effected. After this treatment, the stenotic region can be treated by balloon dilatation, atherectomy and the like to provide increased blood flow through the region.

These and other advantages of the invention will become more apparent from the following detailed description thereof when taken in conjunction with the following exemplary drawings.

BRIEF DESCRIPTION OF THE DRAWINGS

FIG. 1 is an elevational view, partially in section of a vascular catheter which embodies features of the invention;

FIG. 2 is a transverse cross-sectional view taken along the lines 2—2 shown in FIG. 1; and FIG. 3 is an enlarged cross-sectional view of the distal portion of the catheter shown in FIG. 1.

DETAILED DESCRIPTION OF THE DRAWINGS

Reference is made to FIGS. 1-3 which illustrate a vascular catheter assembly 10 embodying features of the invention. The catheter assembly 10 generally comprises a tubular body 11 which has a central lumen 12 adapted to receive a guidewire 13 and a relatively thick cylindrical wall 14 which has a plurality of relatively small diameter lumens 15 disposed longitudinally therein which are adapted to direct fluid through the flow passageways 16. Preferably, the small diameter lumens are equally spaced within the wall 14 about the central lumen 12.

An adapter 17 is provided on the proximal end 18 of the tubular body 11. A first arm 20 thereof is adapted to deliver fluid from a source (not shown) to the small diameter lumens 15 and a second arm 21 is adapted to direct the guidewire 13 into the central lumen 15. A torquing knob 22 is provided on the proximal end of the guidewire 13 to facilitate the guidance thereof through the patient's vasculature. Reference is made to U.S. Pat. No. 4,554,929; U.S. Pat. No. 4,545,390; and U.S. Pat. No. 4,721,117 for a more detailed description of guidewires, which are incorporated herein by reference.

The distal end of the tubular body 11 generally has a tapered body 23 which is formed of a plastic material softer than the material from which the tubular body 11 is made in order to minimize trauma to the arterial lining during the advancement of the catheter through a patient's artery. The tapered body 23 blocks off the distal ends of the small diameter lumens 15.

The length of the vascular catheter will vary depending upon the use thereof. For example, for peripheral uses, lengths may be from about 70 to about 100 cm, whereas for coronary uses lengths may vary from about 120 to about 175 cm. The outer diameter of the tubular body 11 may vary from about 0.05 to about 0.10 inch. Typical diameters of the large diameter inner lumen is about 0.025 to 0.045 inch and for the small diameter lumens 15 are about 0.005 to about 0.025 inch. The flow passageways 16 are preferably uniformly spaced along a length of the tubular body 11 from about 0.5 to 5 cm and the total length of the treating section of the catheter extends from about 2 to about 20 cm.

The tubular body 11 can be made of conventional plastic materials such as polyethylene, polyvinylchloride and the like. Preferably, the stiffness of the tubular body decreases in the distal direction. Stiffness in the proximal portion of the tubular body is desirable from the standpoint of pushability but flexibility is more desirable in the distal portion in order to pass through the patient's tortuous vasculature. The proximal portion can be provided with greater stiffness by making this portion with higher density plastics, e.g. polyethylene, than the distal end. The distal tip is preferably formed of a much softer plastic to avoid trauma to the blood vessel lining when advancing the catheter therethrough.

The flow passageways 16 through the wall of the tubular body can be formed by drilling (e.g., mechanical or laser) or by notching the exterior wall to expose the small diameter lumens. The flow passageways are preferably spiralled about the tubular body of the catheter, as shown in the drawings, to provide a more uniform flow surrounding the catheter.

While the description of the invention herein has been directed to a catheter for the delivery of thrombolytic fluids, it should be obvious that other fluids can be delivered and that other treatments can be performed. Additionally, while only one source for treatment fluid is shown for the small diameter lumens, each of said lumens can be provided with its own source of such fluid and the flow therethrough regulated independently. Other modifications and improvements can be made to the invention without departing from the scope thereof.

What is claimed is:

1. A multilumen vascular catheter for the uniform delivery of fluid containing drugs, therapeutic agents and the like comprising an elongated tubular body having a first lumen for receiving a guidewire to facilitate the advancement of the catheter through a patient's vasculature and a plurality of second lumens, each of said second lumens having in fluid communication therewith a single flow passageway extending through the wall of the tubular body to the exterior thereof with the flow passageways being longitudinally spaced from each other so that a uniform flow of fluid is discharged over a length of the catheter.

2. The vascular catheter of claim 1 wherein the first lumen is centrally disposed along the longitudinal axis of the tubular body.

3. The vascular catheter of claim 2 wherein the plurality of second lumens are disposed about the first lumen.

4. The vascular catheter of claim 1 wherein the minimum cross-sectional area of the flow passageway ranges from about 0.00005 to about 0.0002 in$^2$.

5. The vascular catheter of claim 1 including means at the proximal end of the catheter for directing fluid into the plurality of second lumens.

6. The vascular catheter of claim 4 wherein the minimum cross-sectional areas of each of the flow passageways through the wall of the catheter are essentially the same.

7. The vascular catheter of claim 1 wherein the flow passageways are spaced longitudinally from one another a distance of about 0.5 to about 5 cm.

8. The vascular catheter of claim 1 wherein at least four second lumens are provided.

9. The vascular catheter of claim 1 wherein the elongated tubular body comprises a cylindrical member with an outer wall and a central first lumen for receiving a guidewire, with the plurality of second lumens extending longitudinally through the outer wall.

10. The catheter of claim 1 wherein the flow passageways are radially spaced about the longitudinal axis of the tubular body about 90° from each other so as to be in a spiral orientation.

11. The method of treating a thrombus within a patient's vascular system comprising:
    (a) advancing a guidewire through the patient's vasculature and passing the distal tip thereof through the thrombus to be treated;
    (b) advancing a vascular catheter over the guidewire and urging the distal portion of the catheter into the thrombus; and
    (c) uniformly discharging fluid containing thrombolytic agents through passageways provided in the distal portion of the catheter into the thrombus.

12. The method of claim 11 wherein the fluid flows through the passageways at rates from about 0.1 to about 1.5 cc's per minute.

13. The method of claim 11 wherein the thrombolytic agents are selected from the group consisting of urokinase, streptokinase, and tissue plasminogen activator.

14. The method of claim 11 wherein the treatment is followed by balloon angioplasty or atherectomy procedures.

* * * * *

UNITED STATES PATENT AND TRADEMARK OFFICE
CERTIFICATE OF CORRECTION

PATENT NO. : 4,927,418
DATED : May 22, 1990
INVENTOR(S) : Michael D. Dake and Mark A. Maguire It is certified that error appears in the above-identified patent and that said Letters Patent is hereby corrected as shown below:

Column 1, line 13, after "arterial" and before "have" insert

--system. The systemic use of such therapeutic fluids--

Column 1, line 50 after "plurality" and before "small"

insert --of--.

Signed and Sealed this

Tenth Day of September, 1991

Attest:

HARRY F. MANBECK, JR.

Attesting Officer

Commissioner of Patents and Trademarks